(12) United States Patent
Iwasawa et al.

(10) Patent No.: US 6,475,948 B1
(45) Date of Patent: Nov. 5, 2002

(54) SB-RE COMPOSITE OXIDE CATALYST AMMOXIDATION

(75) Inventors: Yasuhiro Iwasawa, Tokyo (JP); Takafumi Shido, Tokyo (JP); Haichao Liu, Tokyo (JP)

(73) Assignee: Japan Science and Technology Corporation, Kawaguchi (JP)

( * ) Notice: Subject to any disclaimer, the term of this patent is extended or adjusted under 35 U.S.C. 154(b) by 0 days.

(21) Appl. No.: 09/831,407

(22) PCT Filed: Sep. 4, 2000

(86) PCT No.: PCT/JP00/05986

§ 371 (c)(1),
(2), (4) Date: Sep. 7, 2001

(87) PCT Pub. No.: WO01/19511

PCT Pub. Date: Mar. 22, 2001

(30) Foreign Application Priority Data

Sep. 9, 1999 (JP) ............................. 11-256421

(51) Int. Cl.⁷ ................................. B01J 23/00
(52) U.S. Cl. ........................ 502/302; 502/353
(58) Field of Search ................... 502/302, 353

(56) References Cited

FOREIGN PATENT DOCUMENTS

| | | |
|---|---|---|
| JP | 2-257 | 1/1990 |
| JP | 2-95439 | 4/1990 |
| JP | 2-261544 | 10/1990 |
| JP | 4-275266 | 9/1992 |
| JP | 05-148212 | 6/1993 |
| JP | 05-208136 | 8/1993 |
| JP | 06-116225 | 4/1994 |
| JP | 06-279351 | 4/1994 |
| JP | 06-135922 | 5/1994 |
| JP | 06-228073 | 8/1994 |
| JP | 06-287146 | 10/1994 |
| JP | 07-108101 | 4/1995 |
| JP | 07-157461 | 6/1995 |
| JP | 07-157462 | 6/1995 |
| JP | 07-215925 | 8/1995 |
| JP | 07-215926 | 8/1995 |
| JP | 08-057319 | 3/1996 |
| JP | 08-141401 | 6/1996 |
| JP | 09-157241 | 6/1997 |
| JP | 10-043587 | 2/1998 |
| JP | 11-033399 | 2/1999 |
| JP | 11-124361 | 5/1999 |
| SU | 547444 | 2/1977 |
| SU | 698646 | 11/1979 |

OTHER PUBLICATIONS

Youzhu Yuan et al., "Selective Synthesis of Methylal from Methanol on a New Crystalline $SbRe_2O_6$ Catalyst", Chemistry Letters, Mar. 6, 2000, pp. 674–675, CL–000220, The Chemical Society of Japan.

William T.A. Harrison et al., Synthesis, Structure, and Catalytic Properties of the Layered Oxide $SbOReO_4$ $2H_2O$: Location Hydrogen–Atom Positions by Powder Neutron Diffraction, Chem. Matter, 1993, vol. 5, pp. 1631–1635, American Chemistry Society, Japan.

Hiroyuki Watanabe, "Preparation, Crystal Structure, and Electrical Resistivity of $SbRe_2$ $O_6$ with a Re–Re Bond", Journal of Solid State Chemistry, 1998, vol. 138, pp. 245–249, Academic Press, Japan.

*Primary Examiner*—T. A. Solola
*Assistant Examiner*—Joseph Murray
(74) *Attorney, Agent, or Firm*—Ann S. Hobbs; Venable (57) ABSTRACT

An object of the present invention is to provide an ammoxidation reaction catalyst composed of an Sb—Re compound oxide with which ammoxidation into an unsaturated nitrile such as methacrylonitrile or the like can be performed in the presence of a molecular oxygen-containing gas and ammonia, and a method for manufacturing an unsaturated nitrile such as methacrylonitrile or the like from an aliphatic hydrocarbon such as isobutylene, isobutane or the like using this ammoxidation reaction catalyst. An unsaturated nitrile such as methacrylonitrile or the like is manufactured by subjecting an aliphatic hydrocarbon such as isobutylene, isobutane or the like to vapor phase contact ammoxidation with ammonia and a molecular oxygen-containing gas in the presence of an ammoxidation reaction catalyst composed of an Sb—Re compound oxide such as $SbRe_2O_6$ or the like.

3 Claims, 6 Drawing Sheets

SB-RE COMPOSITE OXIDE CATALYST AMMOXIDATION

The instant application is a 371 of PCT/J700/05986 filed Oct. 4, 2000.

TECHNICAL FIELD

This invention relates to an Sb—Re ammoxidation reaction catalyst, and to a method for manufacturing a corresponding unsaturated nitrile such as methacrylonitrile or the like from a lower hydrocarbon such as isobutylene, isobutane or the like in the presence of both ammonia and a molecular oxygen-containing gas using this Sb—Re ammoxidation catalyst.

BACKGROUND ART

An ammoxidation reaction in which ammonia and oxygen were allowed to act on an organic compound and the methyl groups were directly changed into cyano groups is a well-known conventional method for manufacturing an unsaturated nitrile such as acrylonitrile, methacrylonitrile or the like and numerous ammoxidation reaction catalysts have been proposed up to now. For example, proposed catalysts containing molybdenum include an Mo—V—Te-based oxide catalyst (Japanese Laid-Open Patent Application Nos. 02-257, 05-148212, 05-208136, 06-279351, 06-287146, and 07-108101), an Mo—Cr—Bi-based oxide catalyst (Japanese Laid-Open Patent Application Nos. 06-116225 and 07-215925), an Mo—Te-based oxide catalyst (Japanese Laid-Open Patent Application No. 07-215926), an Mo—V—Te—Nb-based oxide catalyst (Japanese Laid-Open Patent Application Nos. 08-57319 and 08-141401), an Mo—V—Sb—Nb-based oxide catalyst (Japanese Laid-Open Patent Application No. 09-157241), and an Mo—Sb—W-based oxide catalyst (Japanese Laid-Open Patent Application No. 07-157462). Many catalysts containing tungsten have also been proposed, such as a V—Sb—W-based oxide catalyst (Japanese Laid-Open Patent Application No. 02-261544), a V—Sb—W—P-based catalyst (Japanese Laid-Open Patent Application No. 02-95439), a V—W—Te-based oxide catalyst (Japanese Laid-Open Patent Application No. 06-228073), a Cr—Sb—W-based oxide catalyst (Japanese Laid-Open Patent Application No. 07-157461) and the like.

Ammoxidation reaction catalysts containing antimony have also been proposed, which include, in addition to those listed above, Sb—Sn-based, V—Sn—Sb—Cu—Bi-based, V—Sn—Sb—Cu—Te-based, and other such oxide catalysts (Japanese Laid-Open Patent Application No. 04-275266), a V—Sb—Ga-based oxide catalyst (Japanese Laid-Open Patent Application No. 06-135922), a Ga—Sb-based oxide catalyst (Soviet Patent Nos. SU547444 and SU698646), V—Sb—Fe-based, V—Sb—Ga-based, and other such oxide catalysts (Japanese Laid-Open Patent Application No. 06-135922), a V—Sb—Te-based oxide catalyst (Japanese Laid-Open Patent Application No. 04-275266), and a V—Sb—O-based oxide catalyst (Japanese Laid-Open Patent Application No. 11-33399). Further, an oxide catalyst containing molybdenum, tellurium, vanadium, and niobium has also been proposed as an ammoxidation reaction catalyst for manufacturing unsaturated nitrites without lowering the yield or degrading the catalyst (Japanese Laid-Open Patent Application No. 11-124361).

Catalysts containing rhenium (Re) exhibit a distinctive activity in regard to the hydrodesulfurization of crude oil and the dehydrogenation and selective hydration of organic compounds, and for these reactions the activity of a rhenium compound is superior to that of a corresponding catalyst containing molybdenum or tungsten, so rhenium compounds are widely used in many industrial processes, such as the refining of crude petroleum products, the metathesis of alkenes and the like. However, for applications related to catalyst oxidation reactions, all that has been reported is that a rhenium compound will react with ethanol and methanol, and will react as a promoter (catalysts for cobalt, molybdenum, vanadium and the like, for instance) in the selective oxidation of alkenes and aromatics.

Meanwhile, rhenium has been found to be an important element in many active ammoxidation reaction catalysts containing antimony (Sb), as mentioned above. It was not known, though, that Sb—Re compound oxides are useful as ammoxidation reaction catalysts for an aliphatic hydrocarbon.

DISCLOSURE OF THE INVENTION

It is an object of the present invention to provide an ammoxidation catalyst for an aliphatic hydrocarbon such as isobutylene, isobutane or the like, and more particularly an ammoxidation catalyst composed of an Sb—Re compound oxide with which ammoxidation into methacrylonitrile or other such unsaturated nitrile can be performed in the presence of a molecular oxygen-containing gas and ammonia, and to provide a method for manufacturing methacrylonitrile or another such unsaturated nitrile from an aliphatic hydrocarbon such as isobutylene, isobutane or the like using this ammoxidation reaction catalyst composed of an Sb—Re compound oxide.

The inventors conducted diligent research aimed at achieving the stated object, learned that because of the electron configuration of rhenium, an oxide of rhenium has the same electrical potential for the purposes of an ammoxidation catalyst as vanadium (V), molybdenum (Mo), and tungsten (W), and arrived at the present invention upon discovering that when a compound oxide of a rhenium oxide and one of the above-mentioned antimony oxides, and particularly two novel compounds, is produced, and this Sb—Re compound oxide is used as an ammoxidation reaction catalyst in the reaction of isobutylene or isobutane in the presence of ammonia and a molecular oxygen-containing gas, methacrylonitrile is produced very efficiently in the presence of a high concentration of oxygen and ammonia.

Specifically, the present invention relates to a catalyst for the ammoxidation reaction of an aliphatic hydrocarbon, composed of an Sb—Re compound oxide (Claim 1), a catalyst for the ammoxidation reaction of an aliphatic hydrocarbon according to Claim 1, wherein the Sb—Re compound oxide is $SbRe_2O_6$ or $Sb_4Re_2O_{13}$ (Claim 2), and a catalyst for the ammoxidation reaction of an aliphatic hydrocarbon according to Claims 1 or 2, wherein the aliphatic hydrocarbon is isobutylene or isobutane (Claim 3).

The present invention also relates to a method for manufacturing an unsaturated nitrile, wherein an aliphatic hydrocarbon is subjected to vapor phase contact ammoxidation with ammonia and a molecular oxygen-containing gas in the presence of an Sb—Re compound oxide catalyst (Claim 4), a method for manufacturing an unsaturated nitrile according to Claim 4, wherein the Sb—Re compound oxide is $SbRe_2O_6$ or $Sb_4Re_2O_{13}$ (Claim 5), a method for manufacturing an unsaturated nitrile according to Claims 4 or 5, wherein the aliphatic hydrocarbon is isobutylene or isobutane, and the unsaturated nitrile is methacrylonitrile (Claim 6), a method for manufacturing an unsaturated nitrile according to any of Claims 4 to 6, wherein the vapor phase contact ammoxidation is carried out under conditions in which the concentration ratio of the aliphatic hydrocarbon, ammonia, and oxygen is 1:(1.5–5):(2–5) (Claim 7), and a method for manufacturing an unsaturated nitrile according to any of Claims 4 to 7, wherein the vapor phase contact ammoxidation is carried out at a high temperature of 400 to 600° C. (Claim 8).

BEST MODE FOR CARRYING OUT THE INVENTION

The catalyst of the present invention for subjecting an aliphatic hydrocarbon such as isobutylene, isobutane or the like to an ammoxidation reaction is characterized by being composed of an Sb—Re compound oxide such as $SbRe_2O_6$, $Sb_4Re_2O_{13}$ or the like. The method of the present invention for manufacturing an unsaturated nitrile such as methacrylonitrile or the like is characterized in that an aliphatic hydrocarbon such as isobutylene, isobutane or the like is subjected to vapor phase contact ammoxidation with ammonia and a molecular oxygen-containing gas in the presence of an Sb—Re compound oxide catalyst.

The Sb—Re compound oxide (double oxide) of the present invention may be any oxide in which metal oxides of antimony and rhenium have formed a compound, but specific examples include $SbRe_2O_6$, $Sb_4Re_2O_{13}$, $SbOReO_4.2H_2O$ and the like. The Sb—Re compound oxide of the present invention may also encompasses metals other than antimony and rhenium, and oxides of these metals, to the extent that the catalytic activity thereof is not compromised.

The method for manufacturing this Sb—Re compound oxide can be any known method for manufacturing a compound oxide, such as mixing and heating metal oxides, and the composition and structure of the compound oxide thus manufactured can be confirmed by examining the crystal structure, valence, and oscillation mode by X-ray diffraction, X-ray photoelectron spectroscopy, or Raman spectroscopy.

The term "aliphatic hydrocarbon" in the present invention refers to an aliphatic hydrocarbon that is a gas at normal temperature, specific examples of which include isobutylene, n-butylene, isobutane, propane, propylene, pentene, pentane, hexene, and other saturated or unsaturated aliphatic hydrocarbons. "Corresponding unsaturated nitrile" refers to an unsaturated nitrile corresponding to the aliphatic hydrocarbon in question, specific examples of which include acrylonitrile, methacrylonitrile and the like.

Examples of the molecular oxygen-containing gas in the present invention include pure oxygen gas, air, and other such oxygen-containing gases. The vapor phase contact ammoxidation in the present invention can be carried out by introducing a raw material gas composed of a mixed gas in which a molecular oxygen-containing gas, ammonia, and a diluent gas have been added to an aliphatic hydrocarbon gas such as isobutylene or the like in the presence of an ammoxidation catalyst composed of an Sb—Re compound oxide, into a fixed bed reactor containing the above-mentioned catalyst. Examples of the diluent gas include nitrogen, carbon dioxide, helium, water vapor, and mixtures of these gases.

The ammoxidation reaction of an aliphatic hydrocarbon such as isobutylene or the like using an ammoxidation reaction catalyst composed of the Sb—Re compound oxide of the present invention is preferably carried out in the presence of an excess of ammonia, such as at a concentration ratio with isobutylene of at least 1:1, and preferably with the ammonia being used in an amount of 1.5 to 5 times as much as the amount of isobutylene, and in the presence of an excess of oxygen, such as at a concentration ratio with isobutylene of at least 2 times, preferably 3 to 5 times as much as the latter. This is advantageous because it increases the methacrylonitrile selectivity and the isobutylene conversion. Also, conducting the ammoxidation reaction at a temperature of at least 400° C., and preferably 450 to 600° C., is advantageous because this also increases the methacrylonitrile selectivity and the isobutylene conversion.

When an ammoxidation reaction catalyst composed of the Sb—Re compound oxide of the present invention is used in an ammoxidation reaction of an aliphatic hydrocarbon such as isobutylene or the like, it is preferable to use a catalyst that has been pretreated with pure helium gas or with helium gas containing 15 vol % ammonia, because this increases the conversion.

The present invention will now be described in more specific terms through examples, but the technological scope of the present invention is not limited to these examples. The synthesis of methacrylonitrile by the ammoxidation reaction of isobutylene and isobutane is used as an example here, and the conversion and selectivity referred to in the examples are expressed by the following equations.

Conversion=(moles of reacted isobutylene or isobutane)/(moles of supplied isobutylene or isobutane)×100

Methacrylonitrile selectivity=(moles of produced methacrylonitrile)/(moles of reacted isobutylene or isobutane)×100

Active component selectivity=(moles of produced methacrylonitrile+moles of produced isobutylene)/(moles of reacted isobutane)×100

EXAMPLE 1

Preparation of Sb—Re Compound Oxide Catalyst 2.8 g of rhenium(VII) oxide ($Re_2O_7$; made by Soekawa; purity: 99.99%) was put in a Teflon autoclave, and 2 ml of deionized water was added. 1.7 g of antimony(III) oxide ($Sb_2O_3$; made by Soekawa, purity: 99.99%) was added to this at room temperature under vigorous stirring, after which the autoclave was sealed and the contents were heated for 24 hours at 200° C., then aged for another 6 days at room temperature. The sample thus obtained was dried under reduced pressure, which yielded $SbOReO_4 \cdot 2H_2O$. This $SbOReO_4 \cdot 2H_2O$ was spray dried and pre-calcined, rhenium (Re) or antimony(III) oxide was added, and this mixture was calcined at 500° C., which yielded a compound oxide catalyst of $SbRe_2O_6$ and $Sb_4Re_2O_{13}$. The crystal structure, valence, and oscillation mode were then analyzed using an X-ray diffraction apparatus (made by Rigaku), an X-ray photoelectron spectroscope (made by Rigaku), and a Raman spectroscope (made by JASCO Corporation), which confirmed that the obtained compound was an Sb—Re compound oxide of $SbRe_2O_6$ and $Sb_4Re_2O_{13}$.

EXAMPLE 2

Ammoxidation Reaction of Isobutylene with Compound Oxide Catalyst

Figure 1:
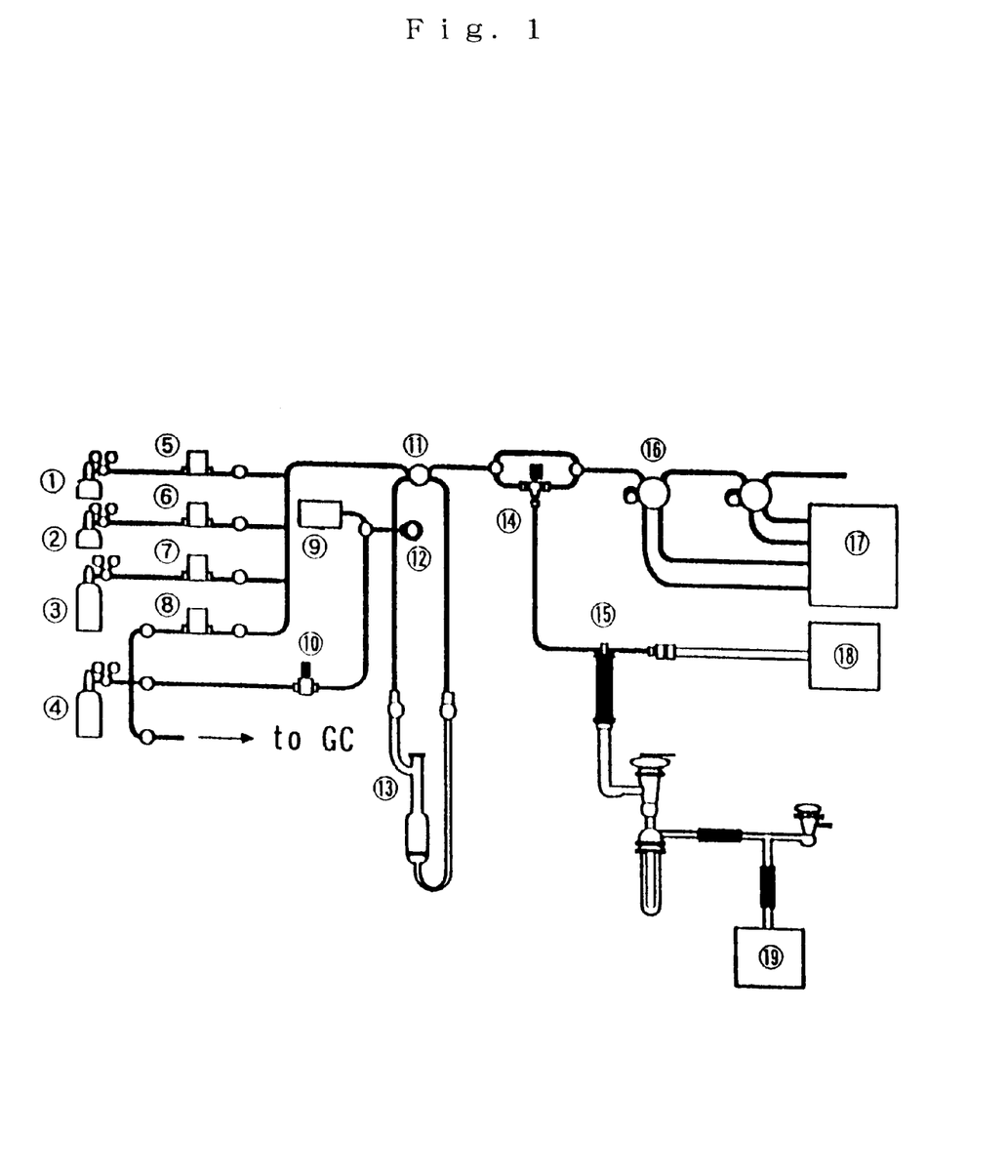
FIG. 1 is a simplified diagram of a reaction apparatus for selective oxidation reaction.

A quartz reaction tube was packed with 0.15 g of either the compound oxide catalyst obtained above, or rhenium (VII) oxide, antimony(III) oxide, or antimony(IV) oxide (used as reference catalysts), and isobutylene was subjected to an ammoxidation reaction using the fixed layer fluidized reactor shown in FIG. 1. In FIG. 1, 1 is an isobutylene tank, 2 is a propane tank, 3 is an oxygen gas tank, 4 is a helium gas tank, 5 is an isobutylene MFC (mass flow controller), 6 is a propane MFC (mass flow controller), 7 is an oxygen gas MFC (mass flow controller), 8 is a helium gas MFC (mass flow controller), 9 is a diaphragm pump, 10 is a flux adjusting valve, 11 is a four-way valve, 12 is a pressure gauge, 13 is a reaction tube, 14 is a needle valve, 15 is a pinhole, 16 is an auto-sampler, 17 is a gas chromatograph, 18 is a mass flow controller, and 19 is a rotary pump.

Figure 2:
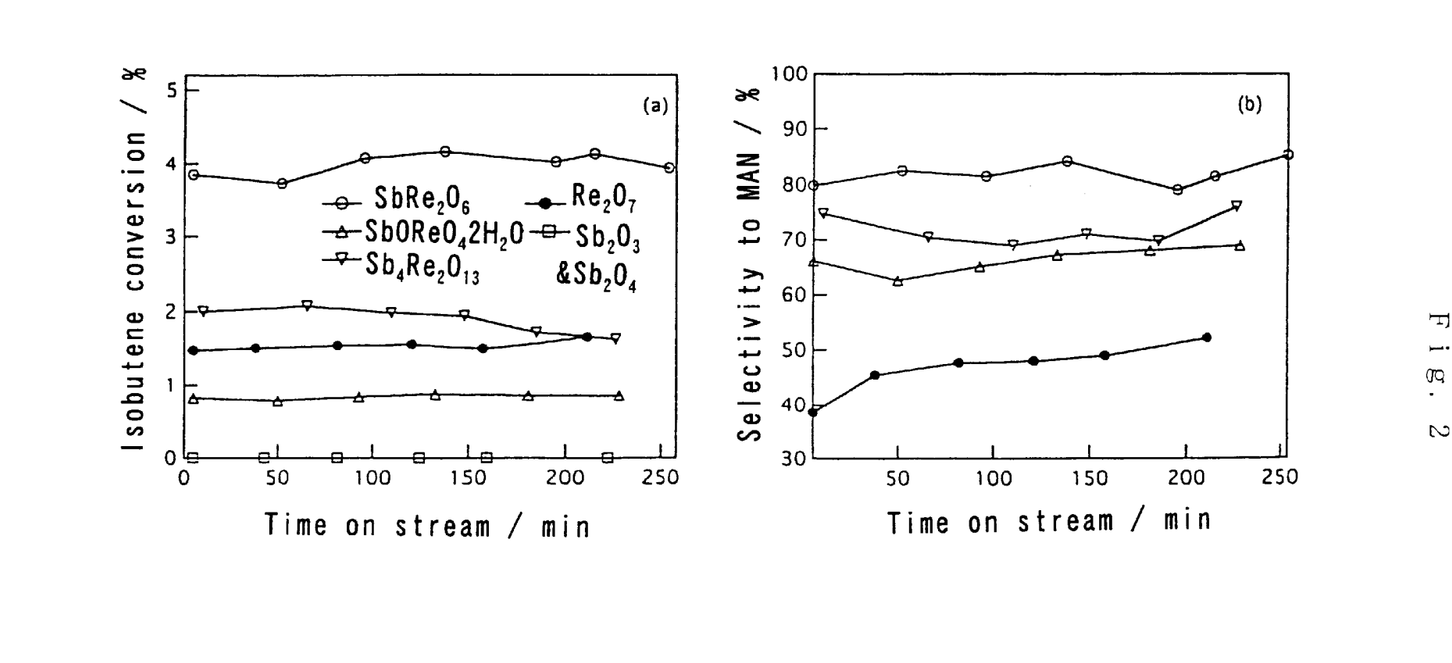
FIG. 2 is a graph of the conversion of isobutylene and the selectivity of methacrylonitrile in an ammoxidation reaction using the Sb—Re compound oxide of the present invention.

The reaction tube 13 packed with the above-mentioned catalyst was adjusted to a temperature of 400° C. by an electric furnace (not shown) controlled by a temperature regulator, after which a mixed gas composed of 10 vol % isobutylene, 15 vol % ammonia, 20 vol % oxygen, and 55 vol % helium was introduced in to the reactor at a gas hourly space velocity (GHSV) of about 20,000/hr by the mass flow controller 18, and an ammoxidation reaction was conducted. The product of this reaction was analyzed by gas chromatography, and the isobutylene conversion and the methacrylonitrile selectivity were calculated at various times from the result of this analysis using the equations given above. These results are shown in FIG. 2. It can be seen from these results that three catalysts ($SbRe_2O_6$, $SbOReO_4 \cdot 2H_2O$, and $Sb_4Re_2O_{13}$) ammoxidized the isobutylene and synthesized methacrylonitrile, but $SbRe_2O_6$ in particular exhibited the highest activity and selectivity. The $Sb_2O_3$ and $Sb_2O_4$ used as reference catalysts, however, exhibited no activity whatsoever under these reaction conditions, which tells us that the $ReO_x$ activity species contributes to the ammoxidation.

EXAMPLE 3

Effect of $SbRe_2O_6$ Pretreatment

Figure 3:
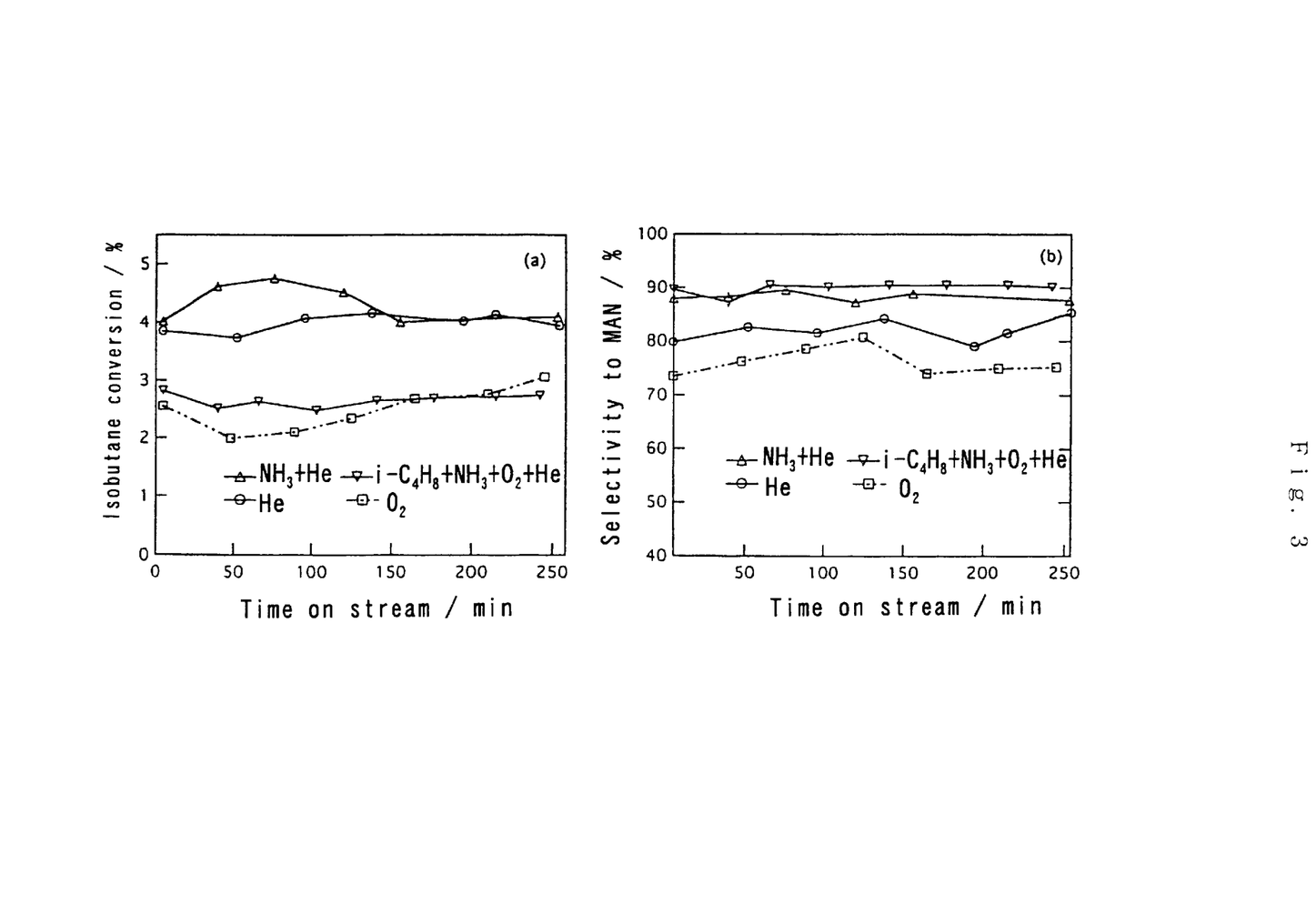
FIG. 3 is a graph of the effect that pretreatment has on the conversion of isobutylene and the selectivity of methacrylonitrile in an ammoxidation reaction using the $SbRe_2O_6$ of the present invention.

The next aspect to be examined was the effect of pretreatment with various gases on the $SbRe_2O_6$ catalyst used in the ammoxidation reaction of isobutylene. The $SbRe_2O_6$ was calcined at 400° C. in the presence of either helium gas containing 25 vol % oxygen, helium gas alone, helium gas containing 15 vol % ammonia, or a reaction gas composed of 20 vol % oxygen, 15 vol % ammonia, and 10 vol % isobutylene equilibrated directly with helium gas. With catalysts obtained by the above calcination, the ammoxidation reaction was conducted in the same manner as in Example 2, and the isobutylene conversion and the methacrylonitrile selectivity were calculated. These results are shown in FIG. 3. It can be seen from these results that pretreatment of the $SbRe_2O_6$ with helium gas alone or with helium gas containing 15 vol % ammonia resulted in an ammoxidation reaction that was very stable and had good activity and selectivity.

EXAMPLE 4

Effect of Ammonia Concentration

Figure 4:
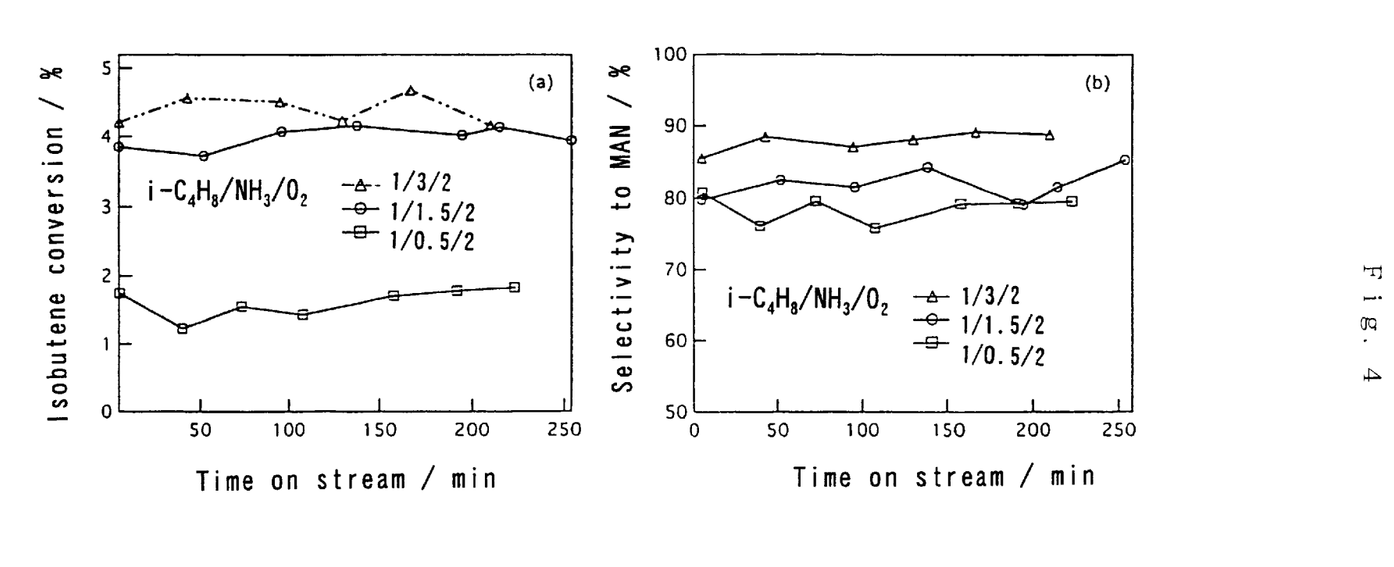
FIG. 4 is a graph of the effect that ammonia concentration has on the conversion of isobutylene and the selectivity of methacrylonitrile in an ammoxidation reaction using the $SbRe_2O_6$ of the present invention.

Ammoxidation reactions were conducted in the same manner as in Example 2 using mixed gases in which the concentration ratios with 10 vol % isobutylene (isobutylene/ammonia/oxygen) were 1/3/2, 1/1.5/2, and 1/0.5/2 respectively, and the isobutylene conversion and methacrylonitrile selectivity were measured. These results are given in FIG. 4. It can be seen from these results that the isobutylene conversion and the methacrylonitrile selectivity both increase along with the concentration ratio of ammonia to isobutylene.

EXAMPLE 5

Effect of Oxygen Concentration

Figure 5:
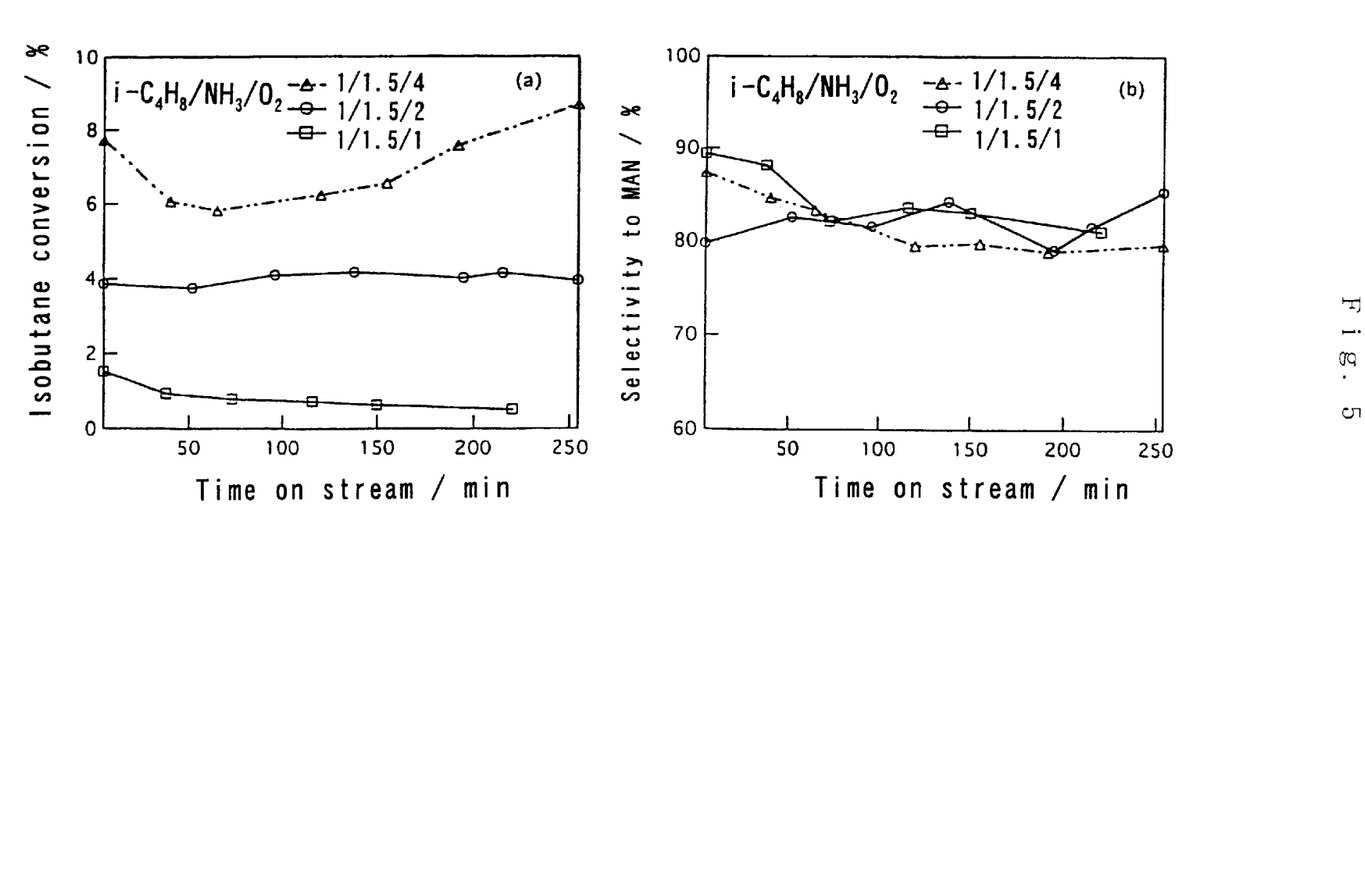
FIG. 5 is a graph of the effect that oxygen concentration has on the conversion of isobutylene and the selectivity of methacrylonitrile in an ammoxidation reaction using the $SbRe_2O_6$ of the present invention.

Ammoxidation reactions were conducted in the same manner as in Example 2 using mixed gases in which the concentration ratios with 10 vol % isobutylene (isobutylene/ammonia/oxygen) were 1/1.5/4, 1/1.5/2, and 1/1.5/1 respectively, and the isobutylene conversion and methacrylonitrile selectivity were measured. These results are given in FIG. 5. It can be seen from these results that the isobutylene conversion increases along with the concentration ratio of oxygen to isobutylene.

EXAMPLE 6

Ammoxidation Reaction of Isobutane

Figure 6:
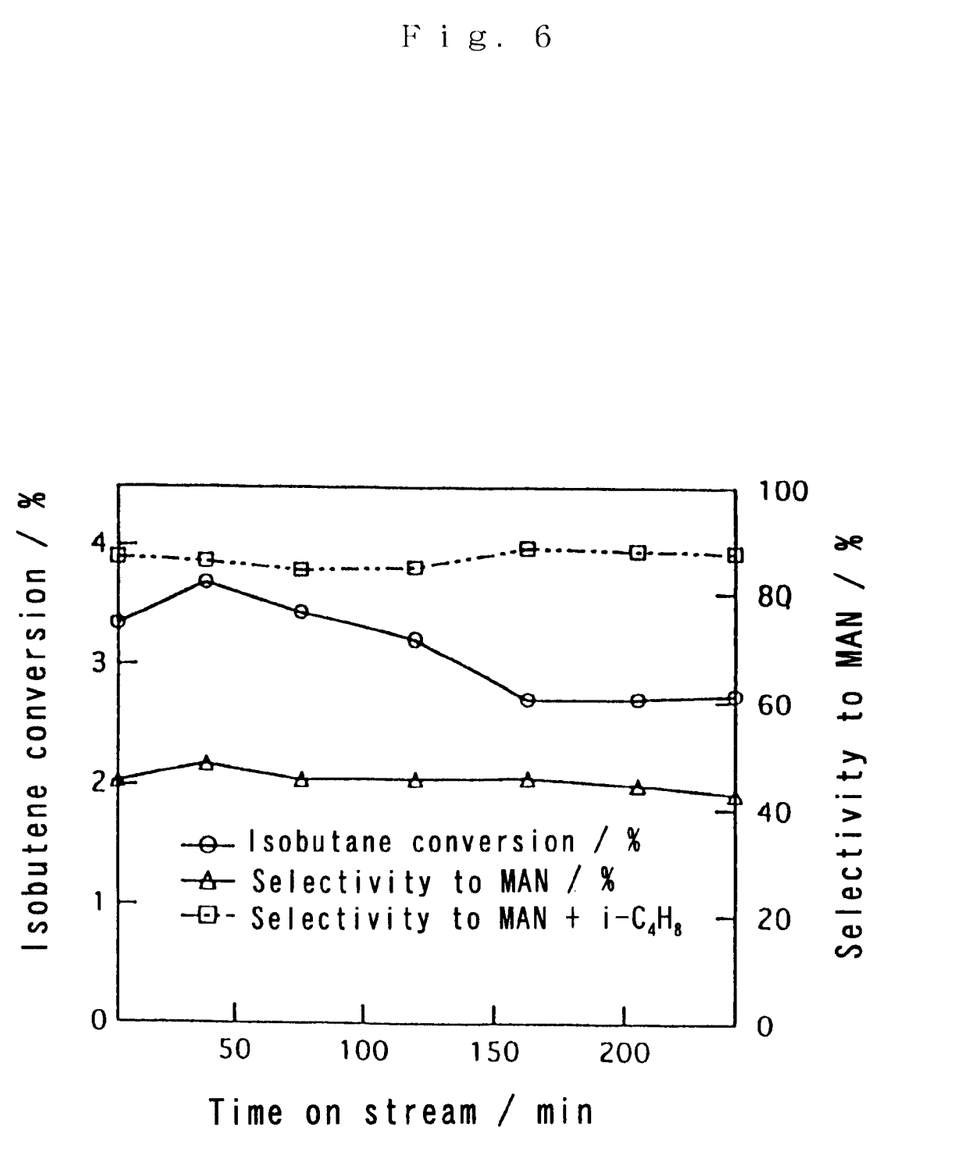
FIG. 6 is a graph of the conversion of isobutylene, the selectivity of methacrylonitrile, and the selectivity of the active component in an ammoxidation reaction using the Sb—Re compound oxide of the present invention.

The reaction tube 13 packed with $SbRe_2O_6$ was adjusted to a temperature of 400° C. by an electric furnace controlled by a temperature regulator, after which a mixed gas composed of 10 vol % isobutane, 15 vol % ammonia, 30 vol % oxygen, and 45 vol % helium was introduced at a gas hourly space velocity (GHSV) of about 5,000/hr by the mass flow controller 18, and an ammoxidation reaction was conducted. The product of this reaction was analyzed by gas chromatography in the same manner as in Example 2, and the isobutane conversion, the selectivity of the active component consisting of isobutylene and methacrylonitrile, and the methacrylonitrile selectivity were calculated at various times from the result of this analysis using the equations given above. These results are shown in FIG. 6. It can be seen from these results that the selectivity of the active component at an isobutane conversion of 3 to 4% was about 85 to 90%, and the methacrylonitrile selectivity was approximately 45 to 50%.

INDUSTRIAL APPLICABILITY

The present invention involves the use of an ammoxidation reaction catalyst composed of an Sb—Re compound oxide, which allows a corresponding unsaturated nitrile such as methacrylonitrile or the like to be manufactured efficiently from a saturated or unsaturated lower aliphatic hydrocarbon such as isobutylene, isobutane or the like in the presence of a high concentration of oxygen and ammonia.

What is claimed is:

1. A catalyst for the ammoxidation reaction of an aliphatic hydrocarbon, characterized by being composed of an Sb—Re compound oxide.

2. The catalyst for the ammoxidation reaction of an aliphatic hydrocarbon according to claim 1, wherein the Sb—Re compound oxide is $SbRe_2O_6$ or $Sb_4Re_2O_{13}$.

3. The catalyst for the ammoxidation reaction of an aliphatic hydrocarbon according to claim 1, wherein the aliphatic hydrocarbon is isobutylene or isobutane.

\* \* \* \* \*